United States Patent [19]

Familletti et al.

[11] Patent Number: 4,849,347
[45] Date of Patent: Jul. 18, 1989

[54] COLORIMETRIC BIOLOGICAL ASSAY

[75] Inventors: Philip C. Familletti, Millington; Judith W. Swanson, Saddle Brook, both of N.J.

[73] Assignee: Hoffmann-La Roche Inc., Nutley, N.J.

[21] Appl. No.: 676,453

[22] Filed: Nov. 29, 1984

[51] Int. Cl.$^4$ .......................... C12Q 1/32; C12Q 1/02; C12Q 1/04; C12Q 1/06
[52] U.S. Cl. ........................................ 435/26; 435/29; 435/34; 435/39
[58] Field of Search ...................... 435/26, 811, 29, 32, 435/34, 39

[56] References Cited

U.S. PATENT DOCUMENTS

| | | | |
|---|---|---|---|
| 3,326,777 | 6/1967 | Babson | 435/26 |
| 3,910,824 | 10/1975 | Cartwright et al. | 435/26 X |
| 4,003,795 | 1/1977 | Lamprecht | 435/26 |

OTHER PUBLICATIONS

Alberts et al., *Molecular Biology of the Cell* (1983), Garland Publishing, Inc., N.Y., pp. 523 and 996.
Carpenter, *Microbiology*, 3rd Ed. (1972), W. B. Saunders Co., Philadelphia, pp. 258–259.
Klebe, "In Vitro", Vol. 20, No. 2 (Feb. 1984), pp. 127–132.
Zolg et al., "In Vitro", Vol. 20, No. 3 (Part I), (Mar. 1984), pp. 205–215.

Primary Examiner—Robert J. Warden
Assistant Examiner—Randall E. Deck
Attorney, Agent, or Firm—Jon S. Saxe; Bernard S. Leon; George M. Gould

[57] ABSTRACT

Lactic acid produced by cells in culture is detected and used in a bioassay to determine cell growth and vitality. Lactic acid is detected by coupling the lactate dehydrogenase conversion of lactic acid to pyruvic acid to a reaction using nicotinamide adenine dinucleotide in reduced form (NADH) to reduce a tetrazolium dye. The process can be used to serve as a bioassay for measuring biologically active compounds, particularly lymphokines.

9 Claims, No Drawings

COLORIMETRIC BIOLOGICAL ASSAY

BACKGROUND OF THE INVENTION

Biological assays have provided a valuable tool in the evaluation of the effect of pharmacologically active compounds including biologically active proteins such as interferons, interleukins, B-cell growth factor or platelet derived growth factor on the growth and viability of a selected cell population. Procedures developed for the bioassay of these types of molecules are usually biphasic. The initial phase consists simply of incubating the substrate cell population with the substance to be tested for a desired period of time. The art has developed several divergent procedures to carry out the second phase of the bioassay, the quantitative analysis of the cellular response to the sample compound.

Generally, the assays of the art include immunomediated assays which are rapid but quantitate only the binding of the molecules to the cell. Another type of assay requires cell staining and visual or microscopic observation of a change in cellular morphology. Such assays are dependent on a subjective evaluation of the results. Still another type of assay system involves use of radioactive metabolites to determine viability. This system is less subjective than the colormetric systems previously described but the processing of numerous samples is time consuming, labor intensive and expensive. Counting the assay cells with the aid of an electronic particle counter to determine cell growth requires large multiples of each sample for accurate results and does not truly reflect the viability of the assay cells.

More recently, colorimetric analysis of cell growth, either by direct staining of a cell monolayer or by cellular dye uptake have been developed. These procedures are less objective then most methods of determining cell growth and many of the steps of the assays are readily adaptable to automation.

An example of one such recently developed system is described by Yeh et al., Journal of Clinical Microbiology, 16, No. 2, 413-415 (1982). In this assay methodology involving a cytopathic effect reduction assay for human interferon, interferon titers were calculated from optical density readings of crystal violet-stained monolayers in an automated spectrophotometer. Multiple samples are handled in such system by utilizing a 96-well microtiter plate.

Another system is described in the paper by Klebe in In Vitro 20, No. 2, 127-132 (1984). In this system nonlethal vital stains comprising two tetrazolium stains identified as MTT and IN tetrazolium are employed. This system is utilized to identify clones derived by genetic mutation or from cell fusions such as for example in the case of producing antibodies secreting hybridomas.

In yet another system described by Zolg et al. in In Vitor, 20 No. 3, 205-215 (1984) lactic acid is used as a metabolic marker for the growth of the desired cell population. This system was utilized to optimize growth of malarial parasites for use in studying this disease. The authors observed that the production of lactic acid by the parasitic cells was dependent upon the developmental stage of the parasites. Detection of the lactic acid obtained from the cell population was accomplished using a commercial lactate test kit involving detecting absorbance at 365 nm of the assay solution.

BRIEF DESCRIPTION OF THE INVENTION

The present invention relates broadly to a new method for detecting lactic acid produced by cells in culture, and in preferred embodiment to coupling of such method to a biological assay for determination of cell growth and cell vitality. The assay of the instant invention determines cell growth in vitro by quantitating the amount of lactic acid (LA) in the cell culture medium. Lactic acid is the final product of glucose metabolism of cells and readily diffuses through the plasma membrane of cells grown in culture. The amount of lactic acid present in the medium reflects the physical state of the cell culture and may be used as a criterion to determine cell growth. Thus, in the practice of the present invention a procedure has been devised to couple the lactate dehydrogenase (LDH) conversion of lactic acid to pyruvic acid to a reaction using nicotinamide adenine dinucleotide (NAD) in reduced form (NADH) to reduce a tetrazolium dye. In this modified form the procedure can be adapted to many cell types and existing biological assays. It can thus be employed to serve as a bioassay for measuring biologically active compounds such as lymphokines e.g. interferons or interleukins, anti-cancer compounds, growth factors such as B-cell growth factor or platelet derived growth factor as well as other compounds which affect cell growth or vitality. In preferred embodiments the present assay is employed to test for the presence of human interleukin 2 and human immune interferon.

The selection of cell lines employed in the practice of the present invention is not narrowly critical. Thus any cell line conventionally utilized as a substrate for biological assay may be utilized in conjunction with the instant novel coupled colorimetric detection procedure. Suitable cell lines include those that are culturable in suspended phase as well as anchor dependents cells which are assayed as monolayers. In general it is preferred to employ cells in concentrations above about 300 cells per micro titer well. This would result in lactic acid concentrations of about 3 micrograms per ml which is approximately the lower limit detectable by the instant assay.

After carrying out the biological assay in a normal manner, samples of the media are obtained and utilized as the substrate for determination of the lactic acid content. Sample size is not narrowly critical but in the most convenient embodiment the bioassay is carried out in micro titer plates using from .005 to .200 ml, most preferably about 0.015 ml of sample is transferred e.g. by automatic pipeter, to a corresponding well in a micro titer plate used for the second phase assay.

A two-part reaction mixture is conveniently employed to carry out the lactic acid determination in accordance with the instant invention. In the first stage a reaction mixture is utilized containing the bioassay sample, and a solution of $\beta$-nicotinamide adenine dinucleuotide (NAD) and a suitable basic buffer solution. Preferably the concentration of the NAD will be in the range from about 0.5 to 2.5 mg/ml, most preferably about 1.6 mg/ml. A suitable buffer solution for purpose of the present invention is obtained by utilizing from 0.01 to 0.05 percent (w/v), most preferably 0.03 percent (w/v) of gelatin in from 0.5 to 0.7 M, most preferably 0.6 M glycine and from 20 to 100 mM, most preferably about 80 mM hydrazine buffer at pH 9.2.

To the aforementioned reaction mixture there is then added a second reaction solution which contains from 100 to 300 units/ml, most preferably about 166 units/ml of lactic dehydrogenase enzyme (LDH), from 0.1 to 0.6 mg/ml, most preferably about 0.50 mg/ml of a tetrazolium dye such as for example p-iodonitrotetrazolium violet and from 0.05 to 0.6 mg/ml, most preferably about 0.33 mg/ml of an electron carrier capable of reducing a tetrazolium dye to a colored formazan. A preferred electron carrier for this purpose is phenylzene methosulfate (PMS).

In general a total of about 0.05 ml of the first solution is used in each well of a micro titer plate as the reaction substrate in conjunction with 0.015 ml of the bioassay sample. The reaction is initiated upon the addition of 0.05 ml of the second solution each well. After sufficient time for reduction of the tetrazolium dye, the reaction is stopped by the addition of a reaction termination solution to each well. A preferably reaction termination solution for purposes of the present invention is a dilute, aqueous mineral acid, most preferably hydrochloric acid. Generally from 0.025 to 0.100 ml, most preferably about 0.05 ml of the termination solution will be employed to stop the reaction in each well.

Determination of the colored formazan compound produced by the coupled reaction is determined by measuring the optical density at a suitable wave length such as for example at 540 nm utilizing a suitable spectrophotometer. By utilizing optical density values derived from standard solutions containing known amounts of lactic acid in corresponding reaction mixtures it is possible to read off the value of the unknown from the standard curves so generated. Thus optial density values were obtained when samples of a lactic acid standard, diluted in phosphate buffered saline (PBS) at the indiated concentration levels were assayed by the coupled colored reaction described above. A solution of PBS served as the background control. The assay samples were added to the first solution in a micro titer plate and the reaction was initiated by the simultaneous addition of the second solution containing the LDH and tetrazolium dye to all the wells. At various times, the reactions were terminated by the addition of 0.35 N hydrochloric acid. The data indicates that a sufficient amount of the p-iodonitrotetrazolium violet dye is reduced to a colored formazan, after the addition of the LDH containing solution to the reaction, to be optically discernable from the control sample within 5 minutes. The rates of formazan production increased proportionately to the amount of lactic acid in the samples during the first 15 minutes of the reaction. Time points greater than 15 minutes, for both the samples and the control, fit a straight line by linear regression analysis and have equivalent slopes, indicating that the rate of color development has become constant and that the reaction may be terminated.

The use of quantitation of lactic acid to determine cell growth in a biological assay is exemplified below by reference to an assay procedure for interleukin 2 and an assay procedure for recombinant human gamma interferon. It is to be understood, however, that the use of the coupled colorimetric procedure of the present invention is not limited in any manner to these specific biological assay systems. Rather the coupled method of the preferred embodiment of the present invention can be employed in conjunction with any biological assay utilizing cultured cells with an end point depending upon determination of either cell growth or cell vitality (or inhibition of cell growth or vitality).

MATERIALS AND METHODS

CTLL, a murine cytotoxic lymphoid line, dependent on interleukin-2 for growth, was maintained on RPMI-1640 medium (Gibco Laboratories) supplemented with 5 percent fetal calf serum (FSC), 25 mM HEPES buffer, 50 µg/ml gentamicin and 20 units/ml of crude IL-2. Jurkat, a human T-cell derived cell line which produces IL-2, was maintained in RPMI medium supplemented with 10 percent FCS, 25 mM HEPES and 50 µg/ml gentamicin. The jurkat and CTLL cell lines were obtained from the Immunex Corporation, Seattle, Washington. HEp-2, a human carcinoma line, was obtained from the American Type Culture Collection, Rockville, Maryland, (CCL 23) and grown in 75 cm$^2$ flasks in Eagles Minimal Essential Medium (MEM) supplemented with 10 percent FCS and 50 µg/ml gentamicin. A phosphate buffered saline (PBS) and HB 101 serum free medium were used in the biological assays for IL-2 and gamma interferon.

EXAMPLE 1

Colorimetric Assay for Recombinant Human Interleukin-2

Biological Assay for Interleukin-2

The procedure to determine the biological effect of IL-2 on cells was carried out in analogy to procedures well known in the art. See for example Gillis et al., Nature, 268, 154–156 (1977). These procedures were modified slightly for the colorimetric analysis procedure of the instant invention. Thus, CTLL cells were removed from the IL-2 containing maintainence medium by centrifugation at 500 xg and washed twice in HB 101 medium devoid of IL-2. The cells were resuspended to a concentration of $2 \times 10^5$ cells/ml in HB101 supplemented with 50 µg/ml of gentamicin. The sample to be titrated was diluted in HB101 in the first well of a row in half-area microtiter plate (Costar 3696) to a final volume of 0.1 ml. Subsequent wells in the row contain 0.05 ml of HB101 and two fold dilutions of the sample were made by transferring 0.05 ml serially to the end of the row. Several wells filled with 0.05 ml of medium, were devoid of IL-2 and served as the negative controls. All wells were seeded with 0.05 ml of the cell suspension and the plate was covered with a plastic lid and incubated for 20 hours at 37° C. in a humidified chamber under atmospheric conditions supplemented with 5% $C_2$.

A standard prepartion of known value and an unknown sample preparation of IL-2 were diluted and incubated for 18 hours with CTLL cells as described above. A 0.015 ml sample from each well was then assayed for lactic acid by the color reaction. In such color reaction, solution A contained 1.6 mg/ml of NAD an 0.03 percent (w/v) gelatin in 0.6 M glycine, 80 mM hydrazine buffer at pH 9.2. A 96-well microtiter plate which contained 0.5 ml of solution A in each well as used as the reaction plate to deterine the amount of lactic acid in the 0.015 ml sample obtained from corresponding wells of the biological assay microtiter plates.

Solution B contained 166 units/ml of LDH, 0.50 mg/ml of p-iodonitrotetrazolium violet and 0.33 mg/ml PMS in water. The addition of 0.05 ml of solution B to each well on the reaction plate started the reaction and after sufficient time for reduction of the tetrazolium dye, the reaction was stopped by the addition of 0.05 ml of 0.35 N HCl to each well. The optical density at 540 nm of each well of the reaction plate was then determined with a microplate spectrophotometer (Artek Model 200). Preparation of all reagents, sample transfers and bioassay microtitrations were carried out by a Pro/Pette liquid handling system (Cetus Corporation).

The average optical density obtained from wells containing CTLL cells without IL-2 was subtracted from all of the values plotted. The results indicate that the growth response of CTLL cells, as determined by the amount of lactic acid in the medium, is directly proportional to the concentration of IL-2. Linear regression analysis of points in the linear portion of the curves yield straight lines for both the samples and standard preparations of IL-2 with correlation coefficients (r) of 0.99 of greater and equivalent slopes (s).

EXAMPLE 2

Interferon Antigrowth Assay

In order to determine the antigrowth effect of interferon by the instant color reaction, confluent monolayers of HEp-2 cells in 75 $cm^2$ flasks were rinsed with PBS and incubated at 37° C. for 10 minutes with 25 ml of a trypsin-EDTA solution to detach the cells from the flask. The cells were removed from the trypsin solution by sedimentation at 500 xg and resuspended in HB101 medium to a concentration of $5 \times 10^5$ cell/ml. A standard cell curve was prepared by adding 0.1 ml of the cell suspension to the first well of a row on a microtiter plate which contains 0.1 ml of HB101 in each well. 2-fold dilutions of the cells were made by transferring 0.1 ml serially to the end of the row. Other wells on the microtiter plate receive 0.1 ml of the cell suspensions and various concentrations of recombinant human gamma interferon. The plate was incubated at 37° C. for 48 hours. A 0.015 ml sample was removed from each well and used to determine the lactic acid concentration by the color reaction as described in Example 1 to quantitate relative cell concentrations.

A standard curve of relative cell concentration verses optical density was obtained. The amount of lactic acid in the medium, as determined by the color reaction, was directly proportional to the amount of HEp-2 cells treated in each well. Optical densities obtained from wells initially treated with $5 \times 10^4$ HEp-2 cells and incubated with recombinant human gamma interferon for 48 hours were positioned on the standard curve and the relative cell concentration extrapolated. Growth inhibition was deterined by comparing the extrapolated cell number in the interferon treated culture to that in the non-treated control (first well). The results indicate that 125 antiviral units of recombinant human gamma interferon inhibit the growth of HEp-2 cells by 32 percent and that 250 units inhibit the growth by 52 percent.

DISCUSSION

It is thus seen that the reaction to specifically convert lactic acid contained in a biological sample to pyruvic acid can be successfully coupled to the reaction to reduce a colorless tetrazolilum dye to a colored formazan. Hydrazine in the buffer prevents the reverse reaction from occurring. Essentially any tetrazolium dye may be used which, in the oxidized state, does not interfere with the enzymatic reaction and is pH compatible. The rate of formazan production is rapid and has been shown to be directly proportional to the amount of lactic acid in the reaction. The entire procedure may be performed in a microtiter plate which allows for many samples to be processed with minimal effort. No additional incubational period of cells and dye is necessary and there is no need to extract the dye from the assay cell with an organic solvent for optical density determinations. Since only a small portion of culture medium is required for the reaction, there is no interference from extraneous color and multiple time points from the same assay can be evaluated without effecting the cells or the incubation conditions.

The antiproliferative effect of interferon on cell types other than HEp-2 can be determined by the color reaction. Suspension cells, as well as other monolayer cells, yield linear standard curves. Cell concentrations as low as 300 cells/well and lactic acid concentrations as low as 3 $\mu$g/ml can be detected by the assay.

Optical densities obtained from the colorimetric analysis of the IL-2 bioassay titrations yielded a linear relationship for IL-2 concentration and cell growth with identical slopes for the sample and standard lines. These criteria were necessary for the determination of IL-2 concentration end points by a parallel line analysis. The $Log_2$ of the X-intercept of a line for each titration represented the maximum dilution of IL-2 that exhibited a positive growth effect on the CTLL cells. End points of the samples were then adjusted to a standard preparation of known value which had been referenced to an IL-2 standard obtained from the Biological Response Modifiers Program, National Cancer Institute, Frederick Cancer Research Facility, Frederick, Maryland and expressed that as units/ml.

Colorimetric analysis of biological samples utilizing the methods of the present invention provides data in a form amenable for computer analysis and BASIC computer programs have been developed in the art which can be rapidly and efficiently analysed as data.

What is claimed is:

1. A method for the determination of lactic acid in a sample which is derived from a medium obtained from a bioassay wherein cells in a culture are treated with test substances which affect cell growth and/or vitality comprising the steps of:
   A. treating cells in a culture medium with test substances which affect cell growth and/or vitality and obtaining a sample;
   B. contacting said sample with a first reaction mixture comprising a predetermined quantity of $\beta$-nicotinamide adenine dinucleotide in a basic aqueous buffer;
   C. adding to the mixture obtained in B a second reaction mixture comprising predetermined quantities of lactate dehydrogenase, a tetrazolium dye and an electron carrier compound;
   D. allowing the reaction to proceed for a sufficient time for reduction of said tetrazolium dye to a colored formazan, the amount of said colored formazan being directly formed and proportional to the amount of lactic acid in said sample; and
   E. determining the optical density of the mixture of D which is directly proportional to the amount of colored formazan present and thereby determining the amount of lactic acid in said sample which is directly proportional to the number of viable cells in said bioassay.

2. The method of claim 1 wherein said test substance is a lymphokine.

3. The method of claim 2 wherein said test substance is a human gamma interferon.

4. The method of claim 2 wherein said test substance is a human interleukin-2.

5. The method of claim 1 wherein said lactic acid is determined quantitatively by comparing the optical density value obtained from the test sample to a standard curve obtained by carrying out the method with varying, known quantities of lactic acid in the samples.

6. A method for the bioassay of a test substance which affects the growth and/or vitality of selected cells which method comprises in combination:
   a. incubating said selected cells with said test substance in an incubation medium;
   B. removing a portion of said incubation medium as a test sample wherein the lastic acid content of said incubation medium is directly proportional to cell growth and/or vitality of said selected cells;
   C. contacting said test sample with a first reaction mixture comprising from about 0.5 to 2.5 mg/ml of β-nicotinamide adenine dinucleotide in hydrazine buffer at pH 9.2;
   D. adding to the mixture obtained in C a second reaction mixture comprising about 100 to 300 units/ml of lactate dehydrogenase, from about 0.1 to 0.6 mg/ml p-iodonitrotetrazolium violet and from about 0.05 to 0.60 mg/ml of phenylzene methosulfate;
   E. allowing the reaction to proceed for a sufficient time for reduction of said-p-iodonitrotetrazolium violet to a colored formazan, the amount of said colored formazan being formed being directly proportional to the amount of lactic acid in said sample; and
   F. determining the optical density of the mixture of E which is directly proportional to the amount of colored formanzan present and thus determining the biological activity of said test substance on said selected cells.

7. The method of claim 6 wherein said reaction in E is stopped by the additional of dilute hydrochloric acid.

8. The method of claim 6 wherein said test substance is a human interleukin 2.

9. The method of claim 6 wherein said test substance is a human gamma interferon.

* * * * *